US010774081B2

(12) United States Patent
Lu et al.

(10) Patent No.: US 10,774,081 B2
(45) Date of Patent: Sep. 15, 2020

(54) INDOLO SUBSTITUTED PIPERIDINE COMPOUND AS ESTROGEN RECEPTOR DOWN-REGULATOR

(71) Applicants: LUOXIN PHARMACEUTICAL (SHANGHAI) CO., LTD., Shanghai (CN); SHANDONG LUOXIN PHARMACEUTICAL GROUP STOCK CO., LTD., Shandong (CN)

(72) Inventors: Jianyu Lu, Shanghai (CN); Charles Z. Ding, Shanghai (CN); Xu Zeng, Shanghai (CN); Huijun He, Shanghai (CN); Shuhui Chen, Shanghai (CN); Lihong Hu, Shanghai (CN); Jiaqiang Dong, Shanghai (CN); Tie-Lin Wang, Shanghai (CN)

(73) Assignees: LUOXIN PHARMACEUTICAL (SHANGHAI) CO., LTD. (CN); SHANDONG LUOXIN PHARMACEUTICAL GROUP STOCK CO., LTD. (CN)

( * ) Notice: Subject to any disclaimer, the term of this patent is extended or adjusted under 35 U.S.C. 154(b) by 0 days.

(21) Appl. No.: 16/345,271

(22) PCT Filed: Oct. 30, 2017

(86) PCT No.: PCT/CN2017/108296
§ 371 (c)(1),
(2) Date: Jul. 8, 2019

(87) PCT Pub. No.: WO2018/077260
PCT Pub. Date: May 3, 2018

(65) Prior Publication Data
US 2019/0337938 A1    Nov. 7, 2019

(30) Foreign Application Priority Data

Oct. 28, 2016  (CN) .......................... 2016 1 0968449

(51) Int. Cl.
C07D 471/04    (2006.01)
A61P 35/00    (2006.01)
(52) U.S. Cl.
CPC ............ C07D 471/04 (2013.01); A61P 35/00 (2018.01)
(58) Field of Classification Search
None
See application file for complete search history.

(56) References Cited

FOREIGN PATENT DOCUMENTS

| WO | 2016097071 A1 | 6/2016 | |
|---|---|---|---|
| WO | 2016097072 A1 | 6/2016 | |
| WO | WO-2016097072 A1 * | 6/2016 | ........... A61K 31/565 |

OTHER PUBLICATIONS

Berge et al., Journal of Pharmaceutical Sciences, Jan. 1977, pp. 1-19.
Remington: The Science and Practice of Pharmacy, 21st Ed., Lippincott, Williams & Wilkins (2005), (Part 1 of 3; pp. 702-798).
Remington: The Science and Practice of Pharmacy, 21st Ed., Lippincott, Williams & Wilkins (2005), (Part 2 of 3; pp. 799-948).
Remington: The Science and Practice of Pharmacy, 21st Ed., Lippincott, Williams & Wilkins (2005), (Part 3 of 3; pp. 949-1057).
Yeung et al., Journal of Medicinal Chemistry, 2010, 53, pp. 5155-5164.
Limanto et al., J. Org. Chem., 2005, 70, pp. 2370-2375.
International Search Report issued in International Patent Application No. PCT/CN2017/108296 dated Jan. 29, 2018.
Written Opinion of the International Searching Authority issued in International Patent Application No. PCT/CN2017/108296 dated Jan. 29, 2018.

* cited by examiner

Primary Examiner — Kortney L. Klinkel
Assistant Examiner — Tori Strong
(74) Attorney, Agent, or Firm — Dilworth IP, LLC

(57) ABSTRACT

Disclosed in the present invention is a type of indole substituted piperidine compounds as an estrogen receptor down-regulator. Specifically disclosed are a compound as shown in formula (I), a pharmaceutically acceptable salt, hydrate or prodrug thereof, a preparation method therefor, a pharmaceutical composition thereof, and a use thereof as an estrogen receptor down-regulator in the treatment of estrogen receptor positive breast cancers.

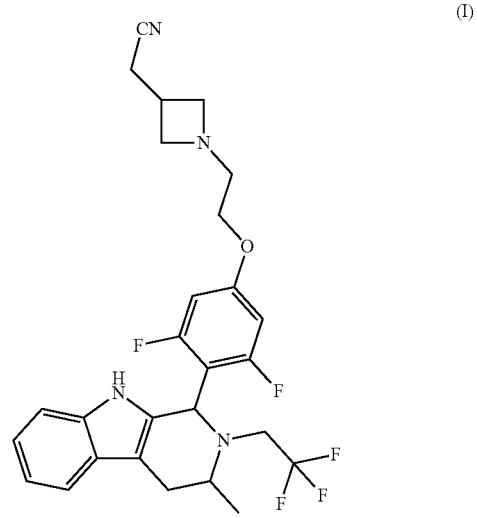

5 Claims, No Drawings

INDOLO SUBSTITUTED PIPERIDINE COMPOUND AS ESTROGEN RECEPTOR DOWN-REGULATOR

CROSS REFERENCE TO RELATED APPLICATIONS

This application claims priority to the Chinese Patent Application CN201610968449.6, filed on Oct. 28, 2016, the content of which is hereby incorporated by reference in its entirety.

FIELD OF INVENTION

The present invention relates to a novel indolo substituted piperidine compound, specifically discloses a compound represented by formula (I), pharmaceutically acceptable salt, hydrate or prodrug thereof, preparation method thereof, pharmaceutical composition thereof and the use thereof as an estrogen receptor down-regulator in the treatment of estrogen receptor positive breast cancer.

PRIOR ARTS

According to statistics of WHO, breast cancer has become the second highest incidence of cancer and the highest incidence of cancer among woman. After years of research, the role of the estrogen-estrogen receptor signaling pathway in the development of breast cancer has been identified; while the estrogen receptor (ER) has also developed into the most important biomarker for breast cancer. According to the expression of estrogen receptor, breast cancer can be divided into estrogen receptor positive breast cancer and estrogen receptor negative breast cancer; among them, estrogen receptor positive breast cancer accounts for more than 70% of the total number of breast cancer patients.

Endocrine therapy (ET), which targets the estrogen-estrogen receptor signaling pathway in breast cancer cells, has become the first choice for the treatment of estrogen receptor-positive breast cancer because it has significant effects and less harmful impacts. ET mostly include the following three treatment methods: ovarian suppression therapy, aromatase inhibitor (AI) and selective estrogen receptor modulator (SERM). Ovarian suppression therapy has less application than the other two therapies because of its poor efficacy and low satisfaction among patients. Early aromatase inhibitors (first and second generation) have low selectivity to target and high toxic side effects; after years of research, the third generation of aromatase inhibitor has greatly improved selectivity, which solves the problem of the early aromatase inhibitor and becomes widely used. Among them, letrozole has been used as a first-line drug for the treatment of estrogen receptor positive breast cancer. The selective estrogen receptor modulator (SERM) acts directly on the estrogen receptor to block the signaling pathway, which has significant effects and a long history of application. As a first-line drug recommended for its priority, tamoxifen which is a most typical selective estrogen receptor modulator has shown significant clinical efficacy in the prevention and treatment of estrogen receptor positive breast cancer.

Although the aromatase inhibitor letrozole and the selective estrogen receptor modulator tamoxifen have shown good efficacy in the treatment of estrogen receptor positive breast cancer, with the application of the two drugs, estrogen receptor positive breast cancer are also becoming more resistant to aromatase inhibitors and selective estrogen receptor modulators. A large amount of studies shows that mechanisms of breast cancer resistance to the above two hormone therapy are not exactly the same. For aromatase inhibitors, estrogen receptors can develop corresponding mutations. The mutated estrogen receptor itself could maintain an agonistic conformation in the absence of estrogen, allowing it to continue to function as a receptor to promote the breast cancer cell proliferation. The resistance mechanism of breast cancer to the selective estrogen receptor modulator tamoxifen is relatively more complicated. Firstly, breast cancer cells can compensate the loss of function caused by the tamoxifen in the estrogen receptor activation function domain-2 (AF-2) by activating the estrogen receptor activation function domain-1 (AF-1). At the same time, breast cancer cells can adapt to the estrogen receptor's conformation after binding with tamoxifen by regulating the structure or concentration of estrogen receptor coactivator, therefore recover the function of the estrogen receptor, which lead to its resistance to drugs.

When treating breast cancer resistant to the two above hormone therapies, selective estrogen receptor down-regulator (SERD) exhibits its characteristic advantage. Mechanistically, selective estrogen receptor down-regulator antagonizes estrogen receptor function, which could greatly accelerate the ubiquitination degradation of estrogen receptors in breast cancer cells (normal or variant), completely blocking estrogen/estrogen receptor signaling pathway, achieving the purpose of inhibiting the growth and proliferation of normal or drug resistant breast cancer cells. Studies shows that selective estrogen receptor down-regulator could effectively inhibit the proliferation of hormone-resistant breast cancer cells. As the only selective estrogen receptor down-regulator on the market, fulvestrant has shown good results in the treatment of hormone-resistant breast cancer, demonstrating the characteristic advantage of selective estrogen receptor down-regulator. However, fulvestrant itself has many problems. Firstly, because of its poor PK property, fulvestrant possesses zero oral bioavailability; besides, fulvestrant has a relatively high blood clearance rate. For both of these reasons above, fulvestrant could only be administrated by intramuscular injection. However, due to its strong lipophilic structure, intramuscularly administrated fulvestrant also possesses serious problem in tissue distribution; in clinical manifestation, only 50% of breast cancer patients who have used fulvestrant show clinical response. Therefore, there is still medical need for research of selective estrogen receptor down-regulator with oral bioavailability.

WO201697071 has reported a selective estrogen receptor down-regulatory compound (II), however it still has disadvantages of molecular instability, high risk of hERG inhibition and unable to cope effectively with cancer cell metastasis.

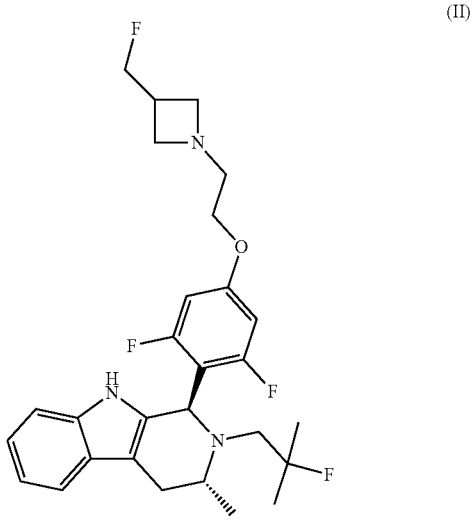 [SMILES: C[C@@H]1Cc2c([nH]c3ccccc23)[C@@H](c2c(F)cc(OCCN3CC(CF)C3)cc2F)N1CC(C)(C)F]

(II)

CONTENT OF THE PRESENT INVENTION

The present invention discloses a compound represented by formula (I), a pharmaceutically acceptable salt, a hydrate or a prodrug thereof,

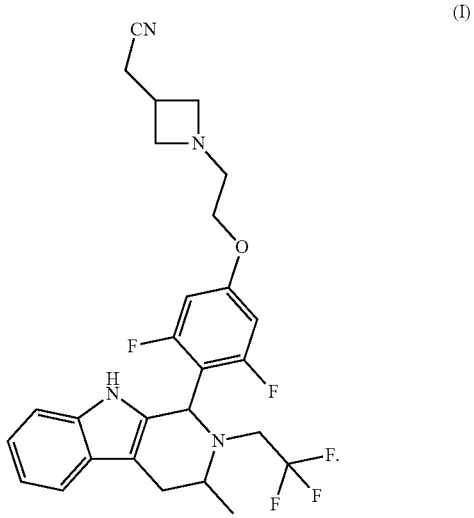 [SMILES: CC1Cc2c([nH]c3ccccc23)C(c2c(F)cc(OCCN3CC(CC#N)C3)cc2F)N1CC(F)(F)F]

(I)

The present invention also discloses a pharmaceutical composition comprising a therapeutically effective amount of the above compound, the pharmaceutically acceptable salt, the hydrate or the prodrug thereof and a pharmaceutically acceptable carrier.

The present invention also discloses a use of the above compound, the pharmaceutical acceptable salt, the hydrate, the prodrug thereof or the pharmaceutical composition thereof in manufacturing a medicament for treating estrogen receptor positive breast cancer.

TECHNICAL EFFECT

Comparing to the prior art, the compound in the present invention has a trifluoroethyl group bind to the piperidine possessing stronger electron attracting property, thus gives the whole molecule a stronger chemical stability; meanwhile, the cyanomethyl structure has a stronger electron attracting ability that further reduces the basicity of the azetidine, thereby lowering the risk of hERG inhibition to the compound of the present invention. The data of in vivo experiment of animals showed that, under the same dosage, the plasma AUC of the compound of the present invention was significantly increased, and the Brain/Plasma ratio was also significantly raised. This shows the compound of the present invention has a superior PK property. It can be reasonably assumed that the compound of the present invention could apply to clinical use with a further lower dosage. Besides, the compound in the present invention could easily pass through the blood-brain barrier, this property gives it a great potential of treating the brain metastasis of the ER positive breast cancer. The compound in the present invention has oral bioavailability and it is an estrogen receptor down-regulatory agent medicament that can be developed into an oral dosage.

DEFINITION AND DESCRIPTION

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., *Pharmaceutical*

Salts," *Journal of Pharmaceutical Science* 66: 1-19 (1977)). Certain specific compounds of the present invention contain both basic and acidic functional groups and can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxy-ethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in a prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in an unsolvated form or a solvated form, including a hydrated form. Generally, the solvated form is equivalent to the unsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, a wedged bond and a dashed bond (   ) are used to indicate the absolute configuration of a stereo center,  and  are used to indicate the relative configuration of a stereo center. When the compound described herein contains an olefinic double bond or other geometric asymmetric centers, E and Z geometric isomers are included unless otherwise specified. Likewise, all tautomeric forms are encompassed within the scope of the present invention.

The compound of the present invention may present in a specific geometric or stereo isomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Optically active (R)- and (S)-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compound of the present invention may contain an unnatural proportion of atomic isotope at one or more than one atom(s) that constitutes the compound. For example, the compound can be radiolabeled with a radioactive isotope, such as tritium ($^3$H), iodine-125 ($^{125}$I) or C-14 ($^{14}$C). All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy,* 21st Ed, Lippincott, Williams & Wilkins (2005), the disclosure of which is incorporated herein by reference.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

All of the solvents used in the present invention are commercially available with no need of further purification. The reaction was generally carried out in an anhydrous solvent under inert nitrogen atmosphere. Proton nuclear magnetic resonance data was recorded on a Bruker Avance III 400 (400 MHz) spectrometer, and the chemical shift was represented by ppm at the low field of tetramethylisilane. The mass spectrum was measured on the Agilent 1200 Series Plus 6110 (&1956A). LC/MS or Shimadzu MS contains a DAD: SPD-M20A (LC) and Shimadzu Micromass 2020 detector. The mass spectrometer is equipped with an electrospray ion source (ESI) operating in positive or negative mode.

The present invention employs the following abbreviations: aq represents water; m-CPBA represents 3-chloroperoxybenzoic acid; eq represents equivalent or equivalence; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; Cbz represents benzyloxycarbonyl, which is an amino protecting group; Boc represents tert-butylcarbonyl, which is an amino protecting group; AcOH represents acetic acid; $NaCNBH_3$ represents sodium cyanoborohydride; THF represents tetrahydrofuran; $Boc_2O$ represents di-tert-butyl dicarbonate; TFA represents trifluoroacetic acid; DIPEA represents diisopropylethyl amine; MTBE represents methyl tert-butyl ether; $Tf_2O$ represents trifluoromethane sulfonic anhydride; TEA represents triethylamine; LAH represents Lithium aluminum hydride; IBX represents 2-iodobenzoic acid; TFAA represents trifluoroacetic anhydride; MSCl represents trifluoromethanesulfonyl chloride; TsCl represents p-methyl benzene sulfonic chloride.

High performance liquid chromatography analysis was performed on a Shimadzu LC20AB system equipped with a Shimadzu SIL-20A autosampler and a Shimadzu DAD of SPD-M20A detector. The column used was an Xtimate C18, (3 m filler, 2.1×300 mm). Method 0-60AB_6 min: a linear gradient was used, starting at 100% A (A: 0.0675% TFA in water) and ending at 60% B (B: 0.0625% TFA in MeCN) over 4.2 min, followed by additional 1 min elution with 60% B. The column was then re-equilibrated for 0.8 min to 100:0 with a total run time of 6 min Method 10-80AB_6 min: a linear gradient is applied, starting at 90% A (A: 0.0675% TFA in water) and ending at 80% B (B: 0.0625% TFA in MeCN) over 4.2 min, followed by additional 1 min elution with 80% B. The column was then re-equilibrated for 0.8 min to 90:10 with a total run time of 6 min Column temperature was 50° C., flow rate was 0.8 mL/min. The Diode Array Detector was scanned from 200-400 nm.

Thin layer chromatography (TLC) was performed on Sanpont-group GF254 silica gel plate. Spots were usually visualized by UV-irradiation, and other methods for visualizing spots on TLC plate were also used. In these methods, 12 (1 g 12 thoroughly mixed in 10 g silica gel), vanillin (1 g vanillin dissolved in 100 mL 10% $H_2SO_4$), ninhydrin (supplied by Aldrich), or a special reagent (25 g $(NH_4)_6Mo_7O_{24}.4H_2O$ and 5 g $(NH_4)_2Ce(IV)(NO_3)_6$ dissolved in 450 mL $H_2O$ and 50 mL conc.$H_2SO_4$) was used to visualize the compound spots. Flash column chromatography was performed on Silicycle 40-63 μm (230-400 mesh) silica gel, by the similar methods disclosed by Still, W. C.; Kahn, M; Mitra, M. *J. Org. Chem.* 1978, 43, 2923-2925. Eluent of flash column chromatography or TLC includes mixed solvents of dichloromethane/methanol, ethyl acetate/methanol and ethyl acetate/n-hexane.

Preparative chromatography analysis was performed on Gilson-281 Prep LC 322 system with Gilson UV/VIS-156 detector. Column was Agella Venusil ASB Prep C18, 5 μm, 150×21.2 mm, Phenomenex Gemini C18, 5 μm, 150×30 mm, Boston Symmetrix C18, 5 μm, 150×30 mm, or Phenomenex Synergi C18, 4 μm, 150×30 mm. At a flow rate of about 25 mL/min, the compound was eluted with MeCN/$H_2O$ with a low gradient, wherein the water contained 0.05% HCl, 0.25% HCOOH or 0.5% $NH_3.H_2O$, and the total run time was 8-15 min.

SFC analysis was performed on an Agilent 1260 Infinity SFC system equipped with an Agilent 1260 autosampler and an Agilent DAD of 1260 detector. The column used was Chiralcel OD-H 250×4.6 mm I.D., 5 μm or Chiralpak AS-H 250×4.6 mm I.D., 5 μm or Chiralpak AD-H 250×4.6 mm I.D., 5 μm. Method OD-H_5_40_2.35 ML column was Chiralcel OD-H 250×4.6 mm I.D., 5 μm, mobile phase was 40% ethanol (0.05% DEA) in $CO_2$, flow rate was 2.35 mL/min, wavelength was 220 nm. Method AS-H_3_40_2.35 ML: column was Chiralpak AS-H 250×4.6 mm I.D., 5 μm, mobile phase was 40% methanol (0.05% DEA) in $CO_2$, flow rate was 2.35 mL/min, wavelength was 220 nm. Method OD-H_3_40_2.35 M: column was Chiralcel OD-H 250×4.6 mm I.D., 5 μm, mobile phase was 40% methanol (0.05% DEA) in $CO_2$, flow rate was 2.35 mL/min, wavelength was 220 nm. Method AD-H_2_50_2.35 ML: column was Chiralpak AD-H 250×4.6 mm I.D., 5 μm, mobile phase was 50% methanol (0.1% MEA) in $CO_2$, flow rate was 2.35 mL/min, wavelength was 220 nm.

Preparative SFC analysis was performed on a Waters Thar 80 Pre-SFC System with a Gilson UV detector. The column used was Chiralcel OD-H 250×4.6 mm I.D., 5 μm or Chiralpak AD-H 250×4.6 mm I.D., 5 μm. A mobile phase of ethanol in $CO_2$ or methanol in $CO_2$ with a low gradient was used to elute the compound at a flow rate between 40-80 mL/min, wherein the ethanol or methanol contained 0.05% $NH_3.H_2O$, 0.05% DEA or 0.1% MEA, and the total run time was 20-30 min.

Compounds are named manually or by ChemDraw® software, the commercially available compounds use their vendor directory names.

DETAILED DESCRIPTION OF THE PREFERRED EMBODIMENT

The present invention will be specifically described below by way of embodiments, but the scope of the present invention is not limited thereto. The content below described the present invention in detail, including disclosure of the specific embodiments. It will be appreciated by the skilled in the art that the order of the reaction step in any reaction scheme may be varied in order to prepare the compound of the present invention, which is also encompassed within the scope of the invention.

Embodiment 1: Intermediate 7

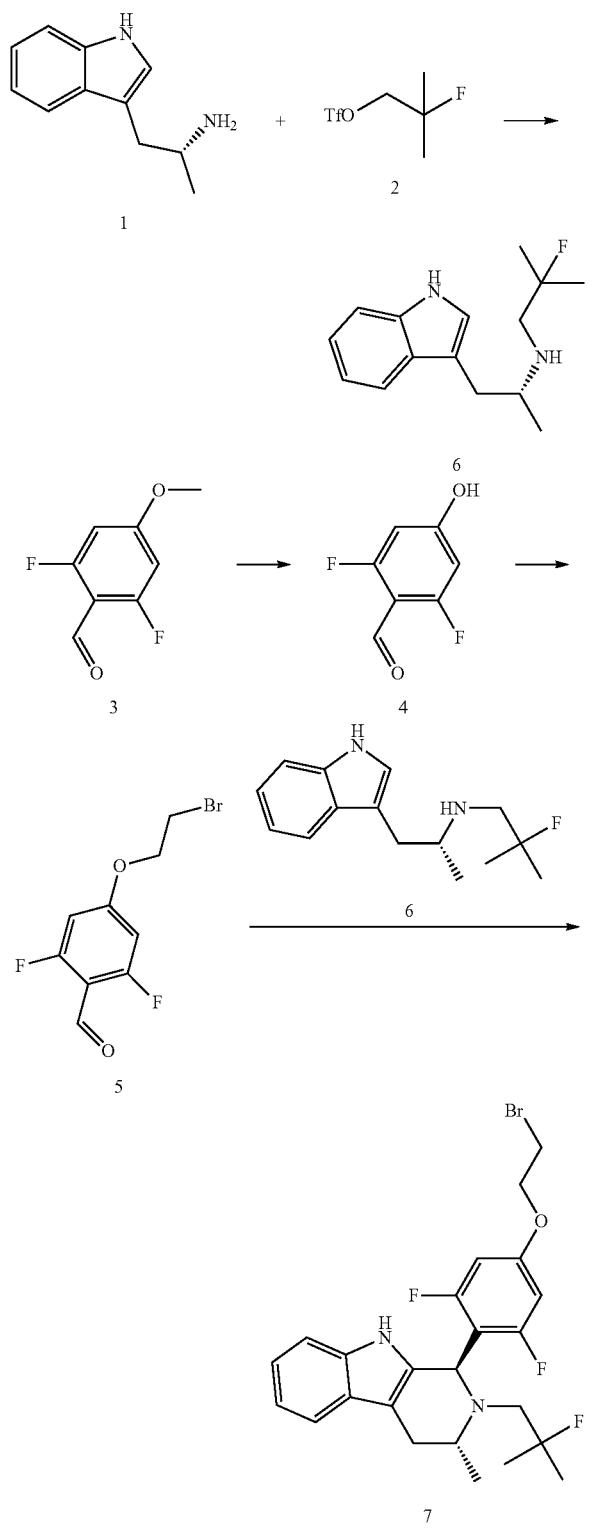

Wherein, the starting material 1 can be prepared by the method reported in the reference (J. Med. Chem., 2010, 53, 5155-5164).

Wherein, the starting material 2 can be prepared by the method reported in the reference (J. Org. Chem., 2005, 70, 2372-2375).

Wherein, the starting material 3 is commercially available.

Step A: Under 25° C., DIPEA (15.6 g, 120.5 mmol, 3.0 eq.) and starting material 2 (18.0 g, 80.3 mmol, 2.0 eq.) were added to the starting material 1 (14.0 g, 40.2 mmol, 1.0 eq.) in dioxane (140.0 ml) solution; the mixture was stirred under the atmosphere of nitrogen at 75° C. for 12 hours. LCMS detected the formation of the product. The reaction was then diluted by 100 ml water and extracted by 150 ml*2 EtOAc, the organic phase after the extraction was washed by 100 ml saline and dried over anhydrous sodium sulfate, followed by filtration and concentration in vacuum thus the crude residue was obtained. The crude residue was purified by silica gel column chromatography (PE:EtOAc=5:1 to 3:1), the intermediate 6 (6.5 g, crude product) obtained was liquid, to be used directly in the next step.

Step B: At −60° C., boron tribromide (5.2 g, 20.9 mmol, 2.0 mL, 3.0 eq) was added into starting material 3 (1.2 g, 7.0 mmol, 1.0 eq.) in dioxane (15.0 ml); the reaction solution was stirred at 25° C. for 12 hours, LCMS detected the reaction was complete, methanol (20.0 ml) was added dropwise into the reaction solution, and the mixture was concentrated. The crude product was then dissolved into EtOAc (100 ml), washed by water (80 ml), dried over anhydrous sodium sulfate and then filtered and concentrated to obtain intermediate 4 (700.0 mg, 4.4 mmol, yield 63.5%).

Step C: At 25° C., cesium carbonate (772.8 mg, 2.4 mmol, 1.5 eq) and 1,2-dibromoethane (445.6 mg, 2.4 mmol, 179.0 uL, 1.5 eq) were added into intermediate 4 (250.0 mg, 1.6 mmol, 1.0 eq) in 7.0 ml acetonitrile. The reaction solution was stirred at 60° C. for 12 hours. TLC (PE:EtOAc=4:1) indicated the reaction was complete. 40 ml Water was added into the reaction solution, then the solution was extracted by EtOAc (40 ml), dried over anhydrous sodium sulfate, filtered and concentrated. The crude product was purified by pre-TLC (PE:EtOAc=4:1); the white solid intermediate 5 (150.0 mg, 565.9 umol, yield 35.8%) was obtained.

Step D: At 25° C., intermediate 6 (187.4 mg, 565.9 umol, 1.0 eq) and acetic acid (101.9 mg, 1.7 mmol, 97.1 ul, 3.0 eq) were added into intermediate 5 (150.0 mg, 565.9 umol, 1.0 eq) in toluene (5.0 ml); the reaction solution was stirred at 90° C. for 5 hours; LCMS indicated the reaction was complete, water (50 ml) was added into the reaction solution, the solution was then extracted by EtOAc (50 ml), dried over anhydrous sodium sulfate, filtered and concentrated. The crude product was purified by pre-TLC (PE:EtOAc=4:1). The intermediate 7 (200.0 mg, 403.7 umol, yield 71.3%) was obtained; LCMS: m/z 495.2 (M+1).

Embodiment 2: Compound (I)

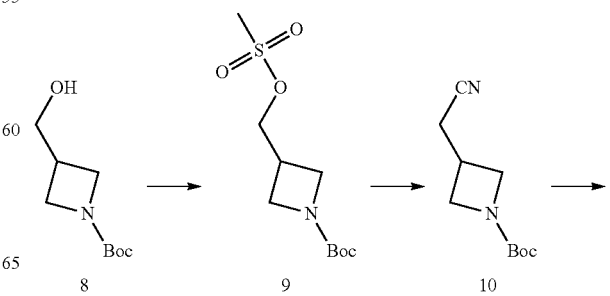

-continued

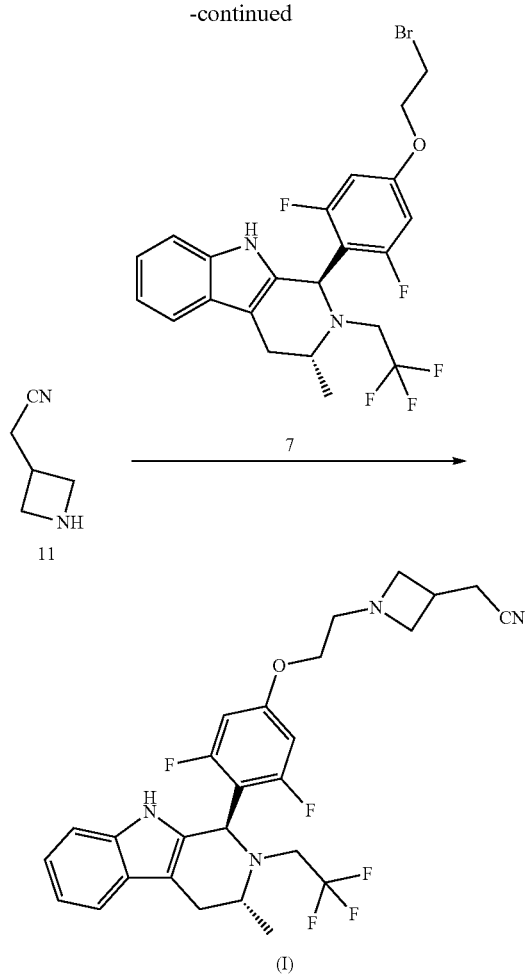

Wherein, the starting material 8 is commercially available.

Step A: At 0° C., starting material 8 (5.00 g, 26.70 mmol, 1.00 eq), TEA (6.75 g, 66.75 mmol, 9.25 ml, 2.5 eq) and dichloromethane (100 ml) were added into a three-necked round-bottomed flask, methanesulfonyl chloride (3.67 g, 32.04 mmol, 2.48 ml, 1.20 eq) was added dropwise under the atmosphere of nitrogen, the mixture was reacted at 0° C. for 2 hours. Water (20 ml) was then added into the mixture, then partitioned, inorganic phase was extracted by dichloromethane 3*50 ml. The organic phases were then combined and washed by saturated saline (50 ml), dried over anhydrous sodium sulfate and then filtered and concentrated, the filtrate was concentrated to obtain product 9 (7.08 g, crude product), to be used directly in the next step.

Step B: Compound 9 (7.09 g, 26.72 mmol, 1.00 eq), dimethyl sulfoxide (70.00 ml), KCN (5.22 g, 80.16 mmol, 3.43 ml, 3.00 eq) were added into a single-mouth round bottom flask under the atmosphere of nitrogen, the yellow suspension solution was reacted at 80° C. for 12 hours. Water (20 ml) was then added into the reaction solution, followed by extraction by MTBE 3*50 ml, the organic phases were combined, dried over anhydrous sodium sulfate, filtered and concentrated to obtain product 10 (5.15 g, 26.24 mmol, yield 98.21%), to be used directly in the next step. $^1$HNMR (400 MHz, DMSO-d6) δ 4.02-3.89 (m, 2H), 3.64-3.48 (m, 2H), 2.86-2.79 (m, 3H), 1.38 (s, 9H).

Step C: Product 10 (3.15 g, 16.05 mmol, 1.00 eq) was added into a single-mouth round bottom flask followed by an addition of 12M HCl (8.03 ml, 6.00 eq), the mixture was reacted at 30° C. for 30 mins. The mixture is concentrated under reduced pressure to obtain product 11 (2.00 g, crude product, hydrochloride) and to be used directly in the next step. $^1$H NMR (400 MHz, methanol-d4) δ 4.27-4.15 (m, 2H), 4.05-3.91 (m, 2H), 3.40-3.19 (m, 2H), 2.90 (d, J=6.8 Hz, 1H), 2.80-2.72 (m, 1H).

Step D: Compound 7 (200.00 mg, 397.38 umol, 1.00 eq), compound 11 (63.23 mg, 476.86 umol, 1.20 eq, hydrochloride) and acetonitrile (10.00 ml) were added into a single-mouth round bottom flask, cesium carbonate (284.84 mg, 874.24 umol, 2.20 eq) was added into the mixture under the atmosphere of nitrogen. The yellow suspension was reacted at 60° C. for 12 hours. Then the reaction solution was filtered, the cake was washed by 10 ml EtOAc, the filtrate was concentrated and separated by preparative high performance liquid chromatography (formic acid) to obtain the product I (30.00 mg, 57.45 umol, yield 14.46%, purity 99.3%). 1HNMR (400 MHz, CHLOROFORM-d) δ 7.62-7.51 (m, 2H), 7.26 (br d, J=6.8 Hz, 1H), 7.19-7.09 (m, 2H), 6.43 (br d, J=10.4 Hz, 2H), 5.28 (s, 1H), 3.94 (t, J=5.2 Hz, 2H), 3.65-3.52 (m, 3H), 3.30-3.19 (m, 1H), 3.16-3.08 (m, 3H), 3.03-2.92 (m, 1H), 2.89-2.77 (m, 3H), 2.69-2.61 (m, 3H), 1.19 (d, J=6.4 Hz, 3H); MS (ESI,M+):541.1.

Experiment 1: Evaluation In Vitro (1) MCF-7 Cell Proliferation Inhibition Assay

Experimental Material:

Substrate RPMI 1640, fetal calf serum, reagent Promega CellTiter-Glo. MCF-7 cell lines were purchased from the European Cell Culture Collection (ECACC). Envision multi-lable analyzer (PerkinElmer).

Experimental Method:

MCF-7 cells were seeded in black 384-well plates, each of the well has 600 cells in 30 ml of cell suspension. The cell plates were placed in a carbon dioxide incubator overnight.

The compound to be tested was diluted by 5 times for 10 concentrations with Epmotion, ie., dilution from 0.25 mmol to 1.28 nmol, and replicated. 198 μl Medium was added to the middle plate, and 2 μl of each well of the gradient diluted compound was transferred to the correspondent position on the middle plate, and then 20 μl of each well was transferred to the cell plate after mixing. Then the cell plate was incubated in a carbon dioxide incubator for 6 days.

25 μl Promega CellTiter-Glo reagent was added into each well of the cell plate, the cell plate was then incubated for 10 mins at room temperature to stabilize the luminescence signal. PerkinElmer Envision multi-label analyser was used for readings.

Data Analysis

The original data is converted to the inhibition rate using the equation (Max−Ratio)/(Max−Min)*100%, the value of IC50 also can be obtained by the curve fitting with four parameters. (by 205 model in XLFIT5,iDBS)

(2) ER Degradation in MCF-7 Cell

Experimental Material:

Substrate RPMI 1640, fetal calf serum, PBS, 16% paraformaldehyde, Triton, confining liquid, estrogen receptor antibody, near0infrared goat anti-rabbit secondary antibody, DRAQ5 dye. The MCF-7 cell lines were purchased from the European Cell Culture Collection (ECACC). Odyssey infrared fluorescence scanning imaging system.

Experimental Method:

The MCF-7 cell was seeded in the black 384-well plate, each of the well has 3200 cells in 30 ml cell suspension. The cell plate were incubated in a carbon dioxide incubator for 4 days.

The compound to be tested was diluted by 5 times with Epmotion for 10 concentrations, ie., fulvestrant was diluted from 0.25 mmol to 0.128 nmol, and the other compound from 2.5 mmol to 1.28 nmol, the replicated. 198 μl Medium was added into the middle plate and 2 μl each well of the gradient diluted compound was transferred to the correspond position on the middle plate, then the compound was transferred 20 μl per well after mixing to the cell plate. The cell plate was then incubated in a carbon dioxide incubator for 20 hours.

50 μl 8% Paraformaldehyde was added into each well of the cell plate, after incubation at room temperature for 30 min, the plate was washed by PBS twice, pat dried and 50 ul PBS containing 0.1% Triton was added, the plate was incubated at room temperature for 15 mins, then washed with PBS for 5 times, pat dried and 50 ul confining liquid was added and incubated at room temperature for 1 hour, pat dried and 50 ul confining liquid containing 0.1% estrogen receptor antibody was added and then left at 4° C. overnight. On the next day, the primary antibody was removed and washed 5 times by PBS, then a confining liquid containing 0.1% near infrared goat anti-rabbit secondary antibody and 0.05% DRAQ5 dye was added, then incubated at room temperature for 1 hour and washed by PBS for 5 times, after pat dried, odyssey infrared fluorescence was used for scanning image system and reading the data.

Data Analysis:

The original data is converted to the inhibition rate using the equation (Max−Ratio)/(Max−Min)*100%, and the value of IC50 can be obtained by curve fitting with four parameters (by model 5 in XLFIT5, iDBS)

TABLE 1

In vitro assay data of the compound of the present invention

| Compound | MCF-7 cell proliferation suppression (nM) | MCF-7 ER degradation $IC_{50}$ intracellular (nM) |
|---|---|---|
| Fulvestrant | 1.77 | 0.71 |
| (I) | 1.17 | 1.13 |

Conclusion:

The in vitro activity of the compound of the present invention is superior to the estrogen receptor down-regulator fulvestrant which has been approved.

Experiment 2: Tissue Distribution Evaluation of the Drug

On the 21th day after administration, select randomly three mice from the drug-administrated group, and collect their plasma samples at different timing, the mice were euthanized near Tmax, and the tumor, brain and breast samples were collected.

The procedure of collecting the plasma and tissue samples are as follows:

Plasma: Blood (60 μl) was collected using a 1.5 ml EDTA-K2 anticoagulation tube, the plasma was obtained after immediately centrifugation at 7000 rpm, at 4° C. for 10 mins, then the plasma simple was stored at −80° C. for drug concentration determination.

Tissue: Brain was collected using a 5 ml cryotube and immediately quick froze in liquid nitrogen. After sampling, tissues were stored at −80° C. for drug concentration determination used for comparing the distribution.

Results are concluded in the Table 2.

TABLE 2 tissue distribution evaluation
Ratio of drug concentration

| Compound to be tested | Dosage (mpk) | Plasma AUC | Brain tissue/plasma |
|---|---|---|---|
| (I) | 10 | 20527 | 13.1 |
| (II) | 10 | 15972 | 5.8 |

Conclusion: At the same dose, the compound represented by formula (I) has better PK property, better brain tissue distribution and better ability of penetrating blood-brain barrier.

The invention claimed is:

1. A compound of formula (I), a pharmaceutically acceptable salt, or a hydrate thereof,

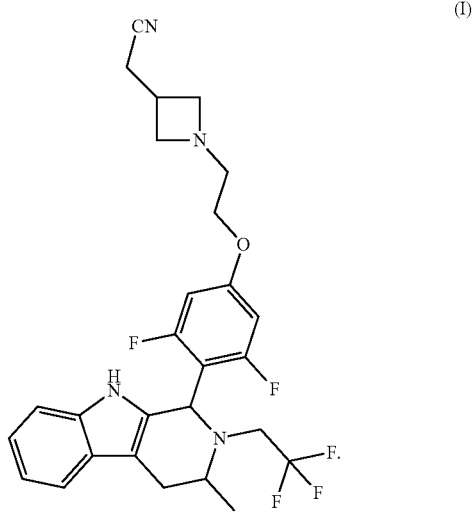 [SMILES: CC1Cc2c([nH]c3ccccc23)C(c2c(F)cc(OCCN3CC(CC#N)C3)cc2F)N1CC(F)(F)F]

(I)

2. A pharmaceutical composition, comprising a therapeutically effective amount of the compound, the pharmaceutically acceptable salt, or the hydrate thereof as defined in claim 1 and a pharmaceutically acceptable carrier.

3. The compound, the pharmaceutically acceptable salt or the hydrate as defined in claim 1, wherein the compound is

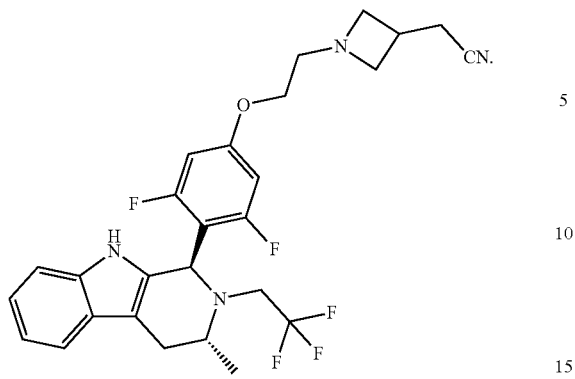

4. A method for treating estrogen receptor positive breast cancer in a subject in need thereof, comprising administering a pharmaceutically effective amount of the compound, the pharmaceutically acceptable salt, or the hydrate thereof as defined in claim 1 to the subject.

5. A method for treating estrogen receptor positive breast cancer in a subject in need thereof, comprising administering a pharmaceutically effective amount of the pharmaceutical composition as defined in claim 2 to the subject.

* * * * *